(12) United States Patent
Wagner et al.

(10) Patent No.: US 11,524,090 B1
(45) Date of Patent: Dec. 13, 2022

(54) PHOTOCATALYTIC LOAD REDUCTION TO EXTEND REACTIVE MEDIA FILTRATION LIFE IN AN AIR PURIFICATION SYSTEM

(71) Applicant: Mainstream Engineering Corporation, Rockledge, FL (US)

(72) Inventors: Andrew L. Wagner, Cocoa Beach, FL (US); Philip Cox, Cocoa Beach, FL (US)

(73) Assignee: Mainstream Engineering Corporation, Rockledge, FL (US)

( * ) Notice: Subject to any disclaimer, the term of this patent is extended or adjusted under 35 U.S.C. 154(b) by 41 days.

(21) Appl. No.: 17/338,773

(22) Filed: Jun. 4, 2021

Related U.S. Application Data

(60) Provisional application No. 63/080,122, filed on Sep. 18, 2020.

(51) Int. Cl.
*A61L 9/20* (2006.01)
*A61L 9/014* (2006.01)

(52) U.S. Cl.
CPC ............... *A61L 9/205* (2013.01); *A61L 9/014* (2013.01); *A61L 2209/12* (2013.01); *A61L 2209/16* (2013.01); *A61L 2209/22* (2013.01)

(58) Field of Classification Search
None
See application file for complete search history.

(56) References Cited

U.S. PATENT DOCUMENTS 10,814,030 B1 * 10/2020 Burnett ...................... A61L 9/22
2015/0306271 A1 * 10/2015 Willette .................. B01D 53/04
422/119

* cited by examiner

*Primary Examiner* — Jelitza M Perez
(74) *Attorney, Agent, or Firm* — Michael W. O'Neill, Esq.

(57) ABSTRACT

A process for using photocatalytic load reduction to extend reactive media filtration life is disclosed for an air purification system. The system consists of three methods of cleaning the air including a UV light, a photocatalyst, and an air purifier. Air first passes through a portion with the UV light and photocatalyst, and then through the purifier. Passing the air first through the UV light and photo catalyst before the purifier reduces the load on the purifier and thus allowing the purifier to operate and clean the air for an extended period of time as compared to the purifier alone.

1 Claim, 6 Drawing Sheets

PHOTOCATALYTIC LOAD REDUCTION TO EXTEND REACTIVE MEDIA FILTRATION LIFE IN AN AIR PURIFICATION SYSTEM

CROSS-REFERENCE TO RELATED APPLICATION

This application claims the benefit of U.S. Provisional Patent Application No. 63/080,122, filed Sep. 18, 2020, which is incorporated by reference here in its entirety.

BACKGROUND

The present invention is directed to extending reactive media filtration life. Particularly, the present invention is concerned with using a photocatalytic load reduction to extend a reactive media filtration life in an air purification system.

In light of the recent COVID19 pandemic there has been a renewed interest in providing air purification systems to remove bacteria and viruses from the air within an enclosed area. In particular, there has been a recent interest for removal of bacteria and viruses from the air that is breathed from a residential home or a commercial space.

Classic air purification systems consists of a type of particulate filter media to filter out the large particles such as dust and the like, some particulate filter media will filter microscopic particles such as smoke. These type of filters are usually located at the return end of a furnace or heating, ventilation, and air conditioning (HVAC) system or a vapor compression (VC) system, i.e., where the air is returning from the enclosed area back into the system for recirculation through the enclosed area again.

Advanced air purification systems will include an ultraviolet (UV) lamp being located normally downstream of the air handler of a HVAC system or a VC system. More advanced air purification systems will not only include a UV lamp, but also a photocatalytic oxidizer in the vicinity of the UV lamp, along with the type particulate filter media located at the return end and sometimes in or proximate the air handler as well to filter out the large particles.

The problem with both the classic and the more advanced air purification systems is the filter media life. The filter media tends to be needing a changing or cleaning frequently in order to maintain filtering capacity and efficiency in the air handling system.

For the foregoing reasons, there is a need for a process to use photocatalytic load reduction to extend a reactive media filtration life in an air purification system in order to extend the time between filter media changes.

SUMMARY

One aspect of the invention is an air purification system to clean and purify air as it passes through normal heating, ventilation and air conditioning (HVAC) operation. The air purifications system is installed inside of the ductwork of an HVAC system after the air handler to clean air before it is returned to the enclosed area, such as a residential home or a commercial space, by the air supply.

The system consists of three methods of cleaning and purifying the air that include an ultra-violet C (UV-C) light, a photocatalyst oxidizer, and an air purifier.

In general operation, air first passes through a portion of the system with the ultra-violet UV light and a baffled design that has photocatalyst oxidizer coating thereon. Then, the air passes through the air purifier.

The invention has many advantages over conventional air purification systems. For instance, UV-C light is lethal to many viruses and bacteria by damaging the DNA and RNA of the organism.

The baffled design increases the UV exposure time and thus the effectiveness of the system. In addition, the UV-C light being emitted onto the photocatalyst oxidizer stimulates the photocatalytic oxidation (PCO) process. That process forms hydroxyl radicals that break down the organic substances by oxidation which reduces bacteria, viruses, and odors, as well as, volatile organic carbons (VOCs) emitted from paints, cleaners, building materials, and cooking.

The invention uses a reactive media to further purify the air. In particular, this reactive media is an activated carbon/potassium permanganate (AC/PP) purifier. This purifier acts as a final air polishing. The activated carbon adsorbs volatile components and odors to further clean the air. The potassium permanganate works as a strong oxidizing agent to provide an additional level of protection beyond the photocatalytic oxidation because it further oxidizes any VOCs.

An object of the disclosure is to disclose at least one implementation that provide for in-duct air purification unit for an HVAC system for reducing and removing air contaminants comprising a chamber with a photocatalytic coating and UV light that operate in an initial chamber that generates reactive hydroxyl radicals followed by a reactive and passive mixed media purifier to polish the air, wherein the initial chamber provides continuous production of hydroxyl radicals to remove contamination and regenerate the purifier to extend the purifier lifetime or reduce its size or capacity. Further, providing for a photocatalytic coating is a light activated oxide that could be modified with metal or non-metals to improve their light activation range. Further, providing for UV light operates between 180-280 nm and the UV light being either mercury vapor lamp or light-emitting diodes. Further providing for a purifier that contains an inert compound such as activated carbon and an oxidizing compound such as a permanganate, peroxide, oxide.

BRIEF DESCRIPTION OF THE DRAWINGS

These and other features, aspects, and advantages of the present invention will become better understood with regard to the following description, appended claims, and accompanying drawings where:

DESCRIPTION

In the Summary above and the Description, and the claims below, and in the accompany drawings, reference is made to particular features (including method steps) of the invention. It is to be understood that the disclosure of the invention in this specification includes all possible combinations of such particular features. For example, where a particular aspect or implementation of the invention, or a particular claim, that feature can also be used, to the extent possible, in combination with and/or in the context of the other particular aspects and implementations of the invention, and in the invention generally.

Figure 1:
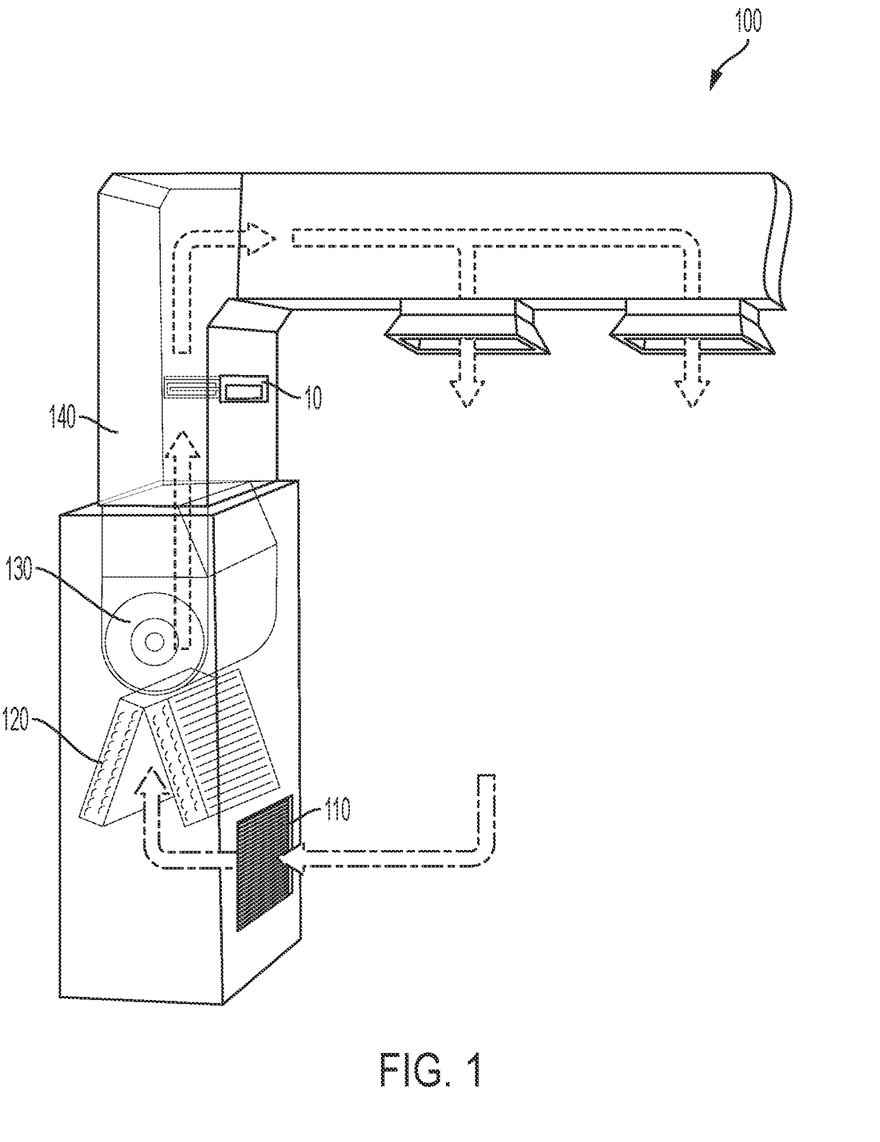
FIG. 1 shows an implementation of the invention installed in a typical HVAC system.

FIG. 1 depicts the overall circulation of air in a typical HVAC system 100 having the improved air purification system according to the disclosure. Contaminated air enters the return air filter section 110 that contains a typically particulate filter media (not shown). This air passes through the return air filter and this filter provides the filtration of the air that would be discharged back into the enclosed area through vents. This air passes through an evaporator 120 in order to remove the heat from the air. Next the air passes through the air handler 130 which includes a blower to push the air into the ductwork 140. The improved air purification unit 10 according to the invention is located after the air handler section 130. The air will pass through the unit 10. While not all of the air will pass through the unit 10 as the unit 10 is sized smaller than the area of the handler, eventually through repetitive passes all of the air within the enclosed area associated with the HVAC system will pass through the unit 10. The air passes through the unit and is purified by the combination of the UV light, photocatalytic oxidation (PCO), and the activated carbon/potassium permanganate (AC/PP) purifier.

Figure 2:
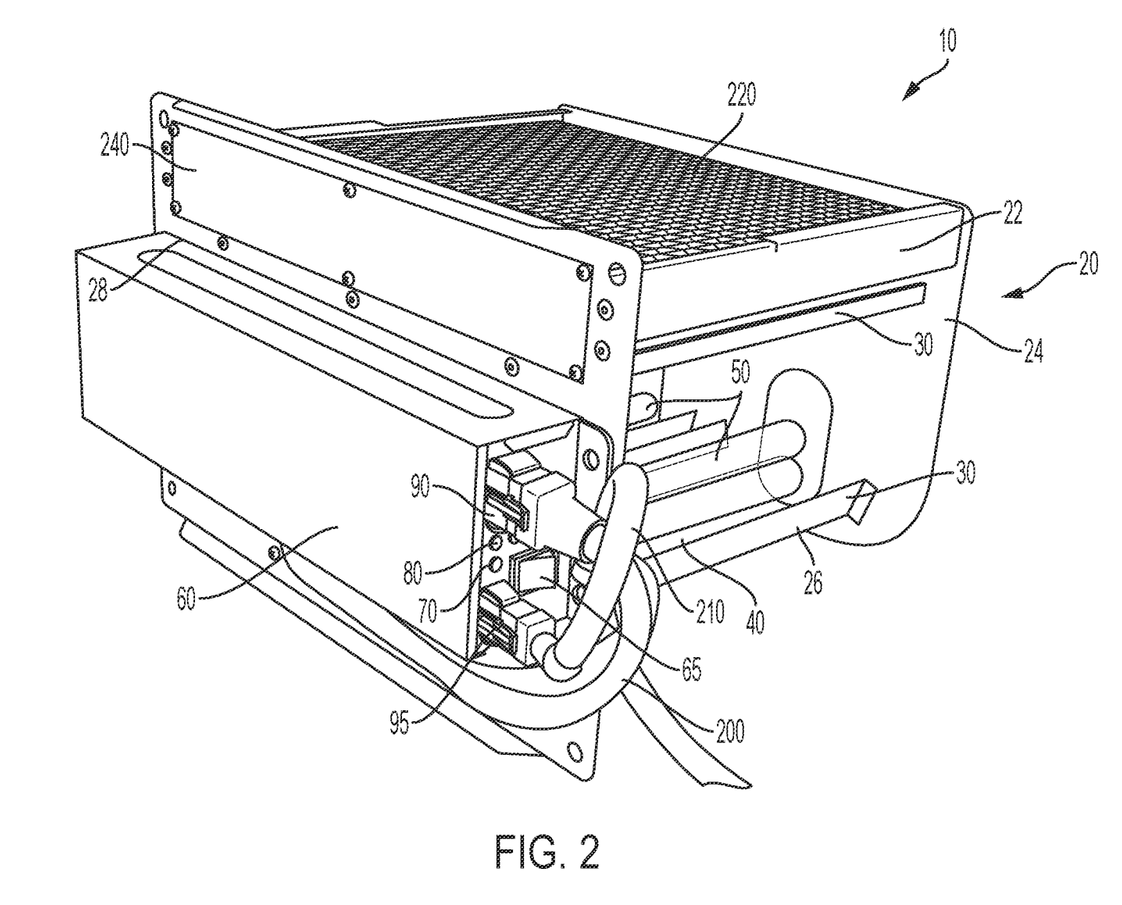
FIG. 2 shows an isometric view of an implementation of the invention.

FIG. 2 depicts an implementation of the self-contained air purification system according to the disclosure. The first portion is a galvanized steel open chamber 20 formed with four sides 22, 24, 26, and 28 with a baffling 30 on one side and the baffling 30 is coated with a titanium dioxide ($TiO_2$) photocatalyst coating 40 that is composed of at least some anatase crystal structure, and may contain some rutile/brookite crystals. The $TiO_2$ coating 40 is made up of particles that are nominally smaller than 100 nm and the total coating thickness is greater than 0.5 microns. The chamber 20 also contains a UV lamp 50, preferably two lamps, which emits primarily in the UV-C spectrum at 254 nm. This germicidal ultraviolet purification lamp is a standard low pressure mercury lamp with a tubular glass envelope. The UV lamp 50 can be coated in order to reduce ozone emittance.

The UV lamp 50 is powered by the electrical ballast 60 that is mounted to one of the sides of the open chamber 20. The electrical ballast 60 contains the needed solid state electronic circuitry that includes an EMI filter to block any electromagnetic interference, a rectifier to convert the AC power to DC power, a power factor correction circuit, a half-bridge resonant output to convert the DC to a square wave voltage with high frequency, and a control circuit that controls the voltage and current across and through the UV lamp 50 respectively so as to provide the proper starting and operating electrical conditions to power the UV lamp 50. In addition, the ballast 60 has a power switch 65 to turn on and off the power to the unit 10. When the unit 10 is on, a green LED 70 is illuminated. Further, the ballast 60 has two receptacles, a power receptacle 90 and signal receptacle 95.

Wire leads 200 will supply power to the unit 10. The unit 10 is capable of operating on multiple voltages, e.g., 120, 208, or 240 VAC single phase at 0.8 A for 120 V and 0.4 A for 240 V.

Wire leads 210 supply a signal to the electrical ballast 60 to turn on or off the UV lamps 50. The signal to energize or de-energize the UV lamps 50 comes from the HVAC system's control unit (not shown). When the UV lamps are energized, the orange LED 80 is illuminated. Preferably, if there are more than one UV lamp being used, than each lamp will have a dedicated orange LED to provide an indicator that the UV lamp is illuminated.

The second portion of the unit 10 is a purifier 220 which is a framed unit with a protective mesh 230 (see FIG. 5) containing particles of activated carbon and potassium permanganate. As air passes through the purifier 220, the activated carbon adsorbs contaminants to further clean the air, while the potassium permanganate works as a strong oxidizing agent to further oxidize any VOCs.

Figure 3:
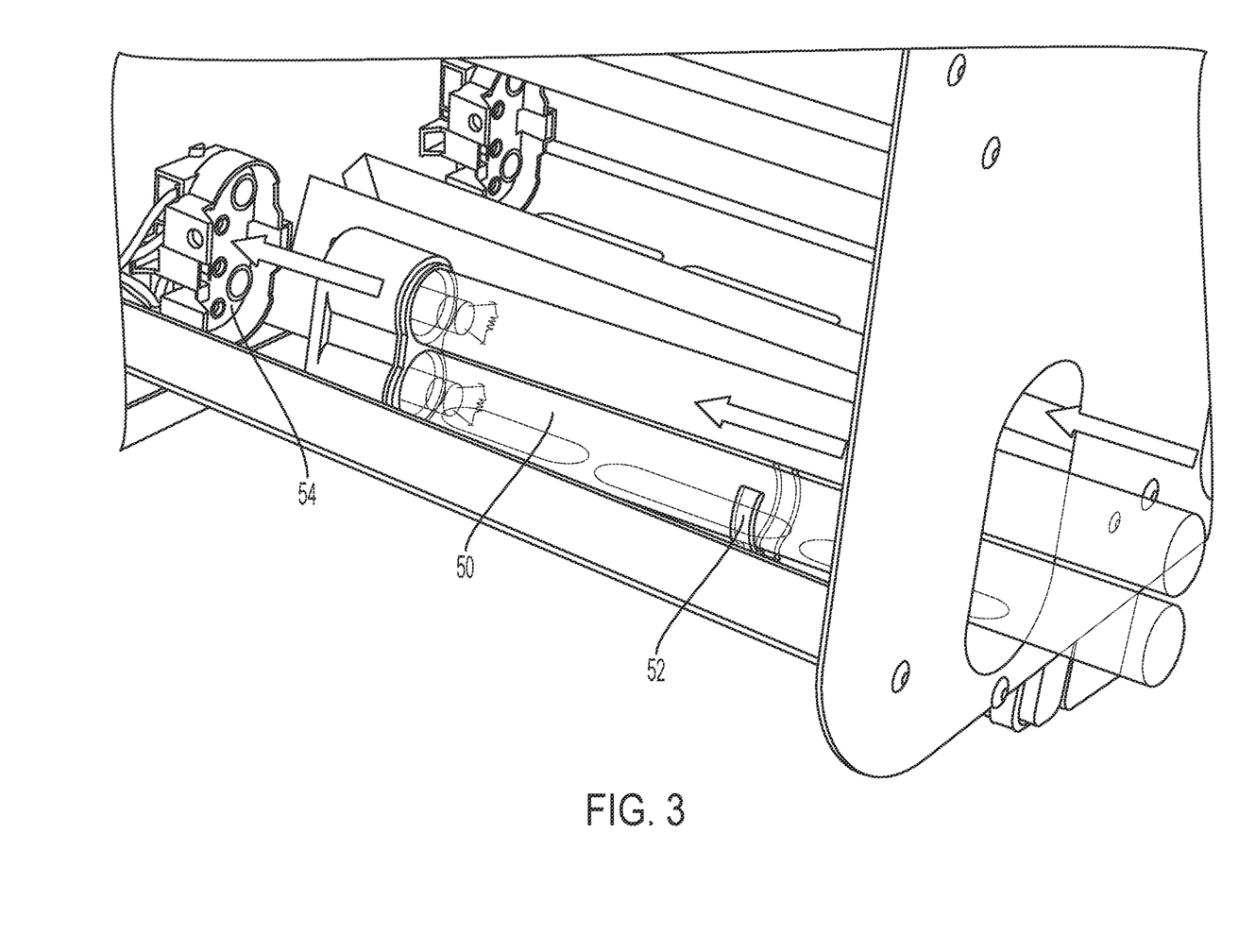
FIG. 3 shows an isometric close up view of the chamber of implementation of the invention.

FIG. 3 shows how the lamp 50 would be installed in the unit 10. The lamps 50 are slid through bulb retainer clip 52 into the lamp receptacles 54 and held in place by the bulb retainer clip 52. Lamp 50 should be replaced annually.

Figure 4:
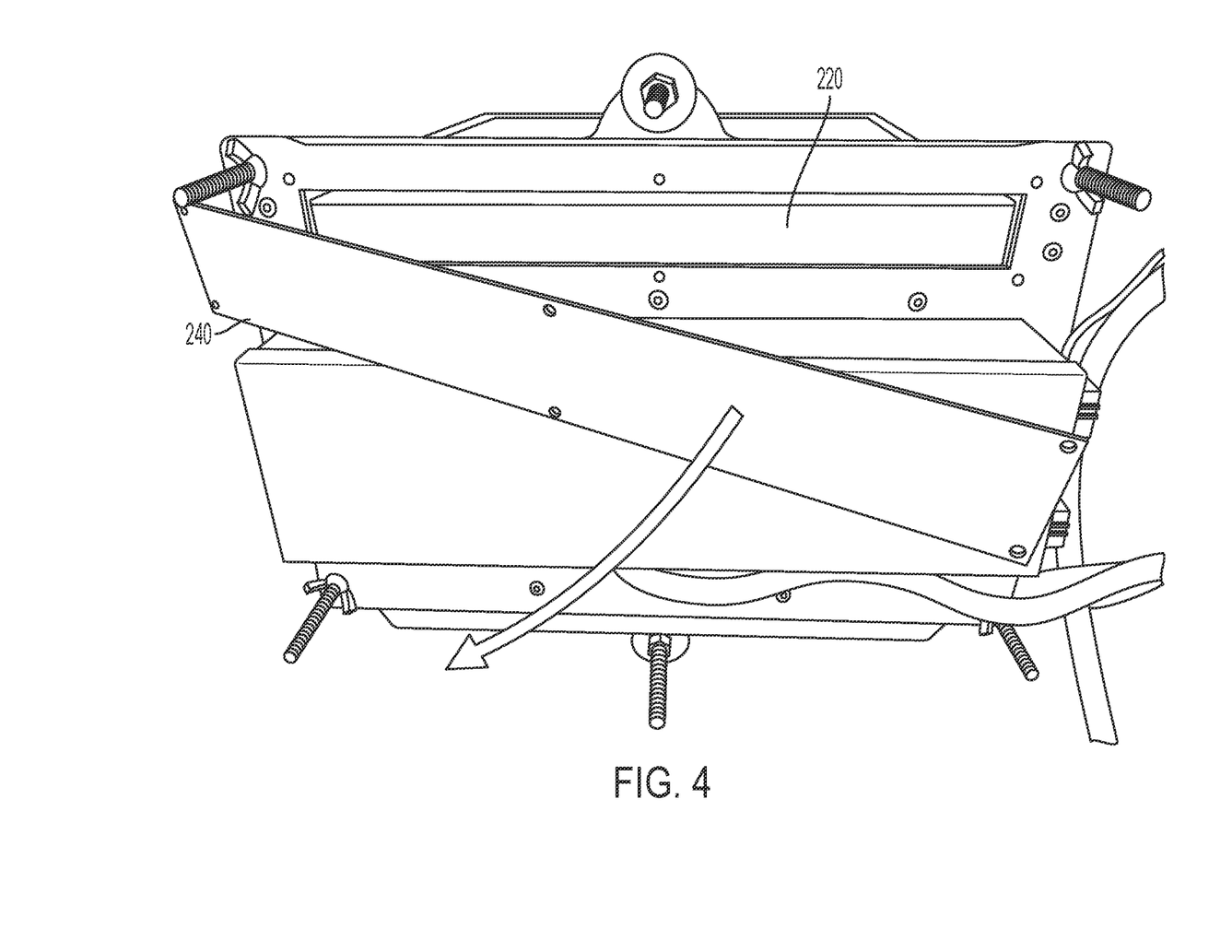
FIG. 4 shows a frontal view of an implementation of the invention.

FIG. 4 shows the access plate 240 removed in order to service the purifier 220. Any type of common fastener can be used to attach access plate 240 to the unit 10. Removal of the access plate 240 is achieved by the removal of the common fasteners that attach the access plate 240 to the unit 10. Purifier 220 should be replaced annually, preferably at the same time as the lamp 50. Further, power should be turned off prior to removing access plate 240. Once the power to the unit 10 is turned off and access plate 240 is removed, then the purifier 220 can be removed by the technician grabbing hold of the purifier 220 and pulling the purifier 220 out from the unit 10.

Figure 5:
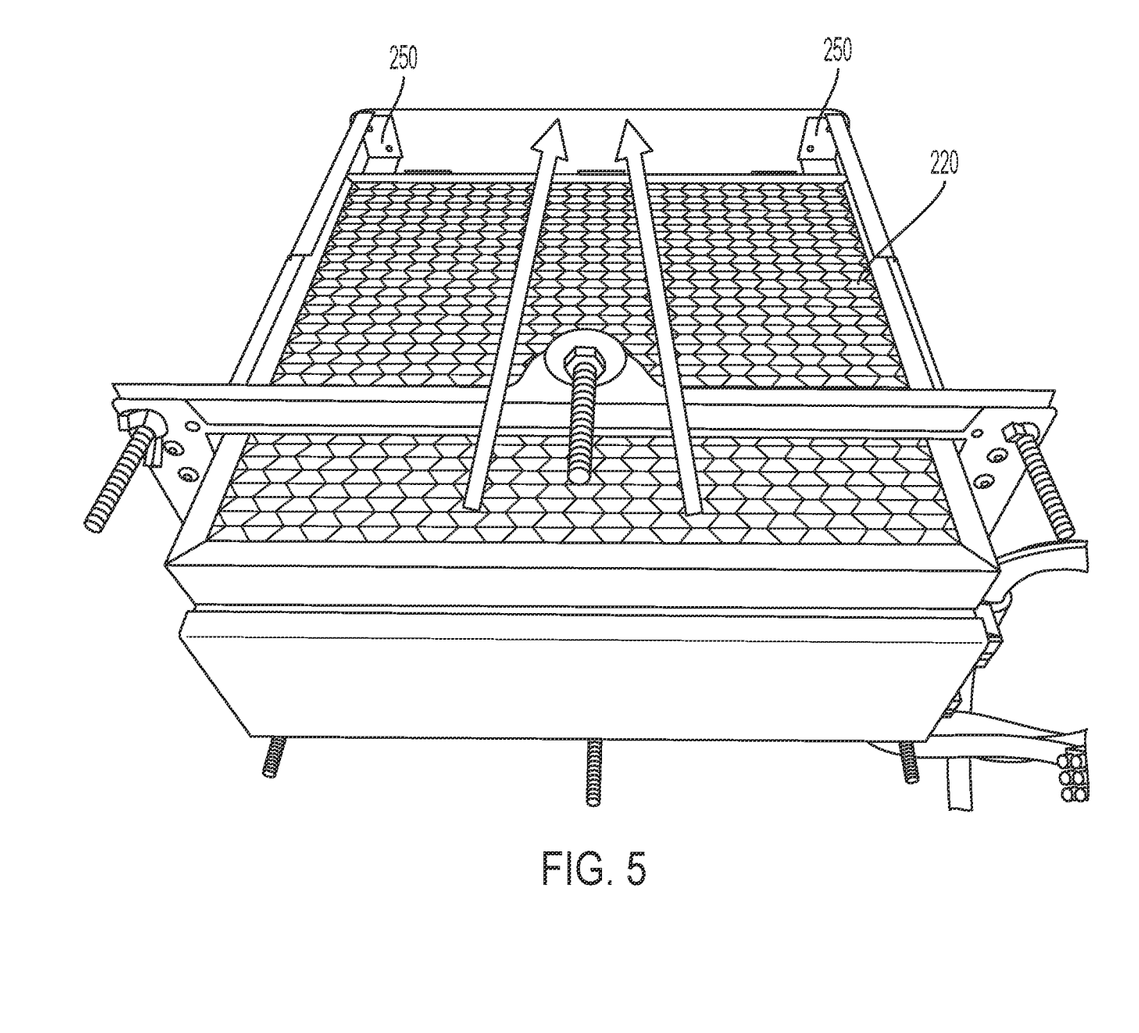
FIG. 5 shows an isometric top view of the purifier partially within an implementation of the invention.

FIG. 5 shows the installation of the purifier 220 either at commission of the unit 10 or at a service call on unit 10 that would be done annually, along with replacement of lamp 50. The purifier 220 is slid into its location by sliding the purifier 220 on the rails 250 as the arrows depict in FIG. 5. The rails 250 are positioned above the chamber 20 that houses the UV lamp 50 and baffling 30. Rails 250 also act as an additional structural support to provide rigidity to the unit 10 when the unit 10 is installed.

Maximum performance is achieved when the unit 10 is located in the air plenum just after, i.e., downstream, of the air handling unit, for example, air handling section 130 in a typical split HVAC system 100. Note that this location is the supply or post-evaporator air side of the air handler, not the return air side. The unit 10 does not replace the traditional air filter located on the return side of the air handler. That traditional air filter's purpose is to filter out particulate matter and dust, while the unit's purpose is to sanitize and purifier the air.

As part of considering the mounting location of the unit 10, the power source location is a factor. Typically the power source for the unit 10 will be from the air handler itself. The unit 10 operates on any AC voltage between 120 and 240 volts. A typical residential AC air handler and heat pump operates on 240 VAC, while a furnace operates on 120 VAC. Fuses should be supplied between the unit and the power source in order to provide over-current protection.

Another consideration that needs to be taken into account when mounting the unit 10 into an HVAC system is accessibility to the purifier 220 for servicing. The purifier 220 should be changed annually. Accordingly, ample space to slide the purifier 220 out of the unit 10 is essential for servicing and thus there should be no obstructions limiting the travel of the purifier 220 in or out of the unit 10.

Ideally the location of the unit 10 should be in the center of the air flow of the ductwork that the unit 10 is being installed therein. That is midway between the sides of the ductwork.

Figure 6:
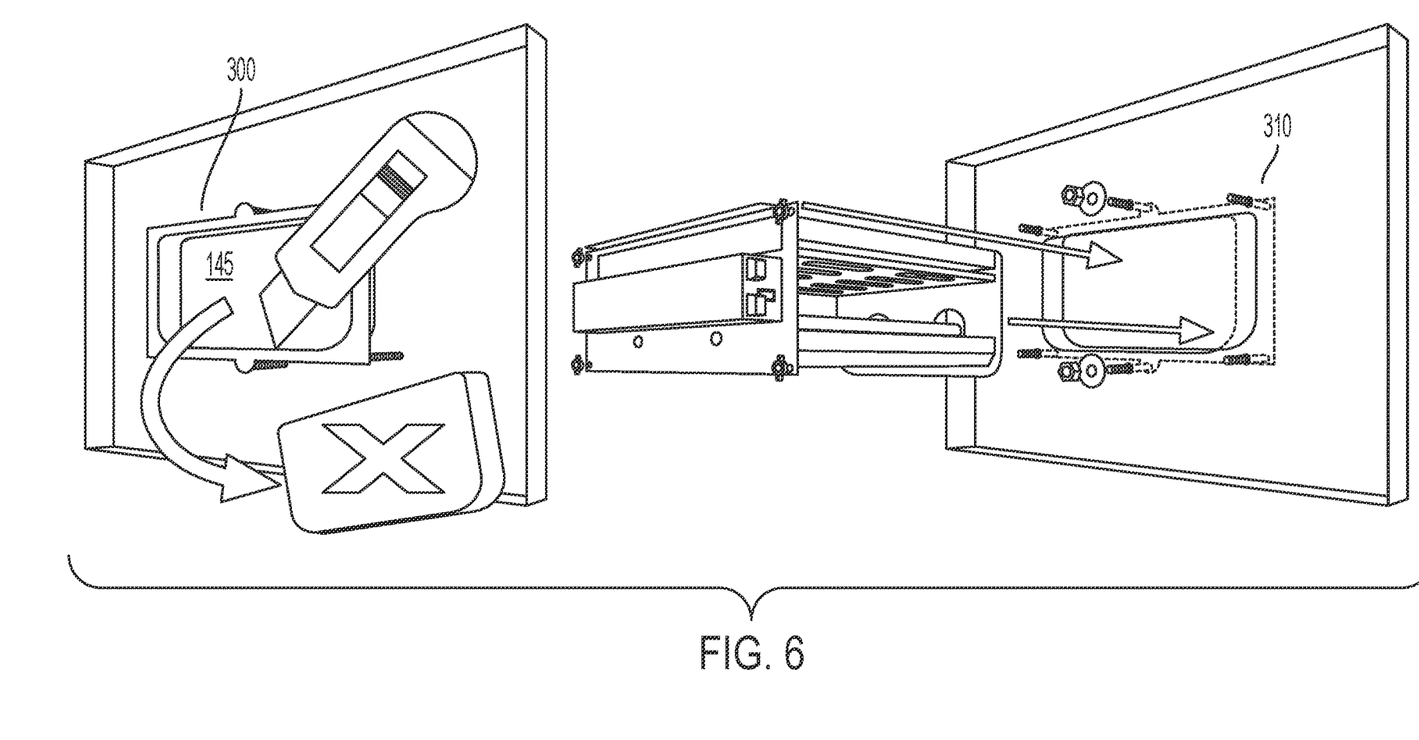
FIG. 6 shows an isometric view for demonstrating how to install an implementation of the invention in the ductwork of a typically HVAC system.

FIG. 6 depicts the installation of the mounting bracket 300 used to install the unit 10 into the HVAC system 100. Prior to install the unit 10 into the HVAC system 100, a technician should determine the mounting location. The technician should first make sure that the ductwork in the proposed mounting location is deep-enough to accommodate the depth of the unit 10. The unit 10 can be mounted in any orientation, e.g., horizontal, vertical, or any angle in between.

If the unit 10 is to be installed into duct board, then mounting bracket 300 is used both as the template for locating the threaded studs 310 and as the flange to support the unit 10 on the duct board. Installation begins by preparing to cut and opening 145 in the duct board for insertion of the unit 10.

The manner to prepare to cut an opening 145 in the duct board starts with first positioning and holding the mounting bracket 300 against duct board with the studs 310 pointing toward the duct board and the mounting bracket oriented to the preferred mounting location and position. Next, enough pressure needs to be applied to the mounting bracket 300 in order for the studs 310 to form an indentation or impression the duct board for initiating the creation of holes in the duct board. Next, the mounting bracket 300 is removed and at the location of the stud marks, a drill, sharp pointed object, or the threaded studs 310 themselves are used to generate the holes in the duct board for the threaded studs 310 to pass through in order for the unit 10 to be secured to the duct board when the mounting bracket 300 become flush with the duct board. Once the needed holes are generated, the threaded studs 310 are inserted into those holes and the mounting bracket itself is used as the template for cutting the needed opening 145 for the unit to be placed inside the planned space in the air supply.

The mounting bracket 300 is now inserted through the opening 145 in duct board to locate the mounting bracket 300 inside of the duct board. Next the thread studs 310 are pushed back through the duct board to face the exterior of the duct board. Fastener can be threaded on to at least two of the threaded studs 310 in order to secure the mounting bracket 300 to the duct board. The mounting bracket 300 should now sit flush with the interior surface of the duct board.

To mount the unit 10 onto the duct board, the unit is slid onto the thread studs 310 that were not used to secure the mounting bracket 310 to the duct board, preferably there will be four remaining threaded studs 310. Next, common threaded fasteners can be used to thread on to the remaining threaded studs 310 and secure the unit to the mounting bracket 310. Wing nuts are a preferred threaded fasteners for these threaded stud 310 because those type fasteners can be loosen and tighten without the use of tools, e.g., loosen by hand.

If the unit 10 is being mounted to metal ductwork, then all that needs to be done is the use the mounting bracket as a template to cut the opening 145. The mounting bracket 300 can be discarded and self-tapping sheet metal screws can be used to secure the unit 10 directly to the sheet metal duct work.

For optimal performance and maximum UV lamp life, the unit 10 should be operated continuously. However using a relay, activated by the G (fan relay) and common wires, the unit 10 can also be operated only when the indoor blower is operating.

The unit 10 can be connected to any AC power source between 120 and 240 VAC. Preferably that power should be drawn from the air handler or furnace power source downstream of the air handler or furnace breaker, however any AC power source from 120-240 VAC can be used.

To use the preferred power source, another hole can be drilled into either the duct board or sheet metal duct work proximate the unit 10. A rubber grommet can be used to seal and protect the wire leads 200 as they are passed through duct work of the air handler. To prevent any strain on the wire leads 200, a securing strap can be used.

The power source must be fused. One or two fuses must be used depending on the voltage. If using 120 VAC, then one fuse on the hot wire is needed. If using 240 VAC, then a fuse for each lead is needed. The fuses should be connected between the power source and the wire leads 200 downstream of any disconnect.

A verification concerning the operation of the unit 10 should be conducted by the technician once unit 10 is successfully installed or serviced. First, the unit 10 should be turned on using the power switch 65. When the unit 10 is on, green LED 70 should be illuminated. Likewise, the orange LED 80 should be illuminated which indicates that the UV lamp 50 is operating properly.

As mention above, the purifier 220 should be replaced annually. The fasteners that secure the access plate 240 to the unit 10 need to be removed and then the access plate 240 can be removed to expose the purifier 220. See FIG. 4. Next, the old purifier 220 is slide out and a new purifier 220 is slid in using the rails 250. The access plate 240 is replaced and the fasteners holding the access plate 240 are re-inserted into the unit 10.

It is suggested that the UV lamp 50 be replaced annually. To perform this operation, the technician should confirm that the unit 10 is operating properly by observing whether the green LED 70 is illuminated. Power to the unit 10 should be turned off by turning the power off at the breaker powering the unit 10. Next the wire leads 200 are unplugged from the electronic control module 60. Next the unit 10 is removed from the duct work the unit 10 was secured thereto. The UV lamp 50 is removed by sliding it out of the lamp receptacle 54 and through the end of the unit 10.

At this time, an inspection of the $TiO_2$ coating 40 should be performed and the coating should be cleaned with a damp cloth to remove any dust and debris. The rest of the unit 10 can be cleaned also with a damp cloth.

A new UV lamp 50 is installed by sliding through the end of unit 10 through the clearance holes. The UV lamp 50 is secured to the unit 10 when the end portion is within the lamp receptacle 54 and bulb retainer clip 52. The unit 10 is then reinstalled into the duct work of the HVAC system 100. The wire lead 200 is reattached to the unit 10 and the breaker is turned back on. If all is operating correct, then green LED 70 and the orange LED 80 should be illuminated.

During operation air flows through the chamber and the UV lamp irradiates the $TiO_2$ coating and causes it to catalytically react with moisture in the air to make hydroxyl (OH) radicals which will then react and oxidize contaminants, e.g., volatile organic carbons, odors, into products such as carbon dioxide ($CO_2$) and water ($H_2O$). The combination of the UV light and the hydroxyl radicals will also deactivate bacteria and viruses by damaging their DNA and RNA. The $TiO_2$ photocatalytic coating 40 acts as a catalyst and is not consumed during the formation of hydroxyl radicals. This allows for a continuous supply of reactive hydroxyl radicals as long as the UV lamp 50 is on and there is moisture in the air.

Since the unit is 10 placed after the air handling section on the supply side of the air handler the air has been cooled for the house and will be fully saturated with moisture. This allows for the maximum generation of hydroxyl radicals during standard operation, which improves the effectiveness of the unit.

Hydroxyl radicals have a lifetime between 0.01 to 1 second. In normal residential HVAC operation airflow can be estimated to be around 400 cubic feet per minute per ton of cooling capacity with a recommend air velocity of 120 inches per second. Thus the hydroxyl radicals will react within the baffled zone, i.e., chamber 20 with baffling 30, and may reach the AC/PP purifier 220 within their lifetime and dissipate well before entering the home.

After passing through the chamber 20, air then passes through the AC/PP purifier 220 where remaining organic species are further oxidized by reaction with potassium permanganate, which produces oxidation byproducts including carbon dioxide, magnesium oxide ($MnO_2$) solids, water, and potassium cations. This chemical reaction consumes the reactive potassium permanganate and converts it into benign powder that no longer has a beneficial effect on the air that passes through it. Thus potassium permanganate in the purifier has a finite lifetime and must be periodically replaced.

The AC/PP purifier 220 also contains granules of porous activated carbon which act to adsorb contaminants onto the particle surface. The larger granules are used to reduce pressure drop from gas flow through the purifier. They also provide the benefit of reduced dusting during operation to improve safety in the high flow of an HVAC system. The activated carbon works based on surface interactions by both induced dipole and Van der Waal forces. The activated carbon attracts molecules of all types, not just contaminants that can be oxidized, onto the porous surface. Once the pores are full of contaminants, they will only adsorb contaminants with stronger surface interactions, e.g., phenols will adsorb more strongly than alkyl halides, replace those with weaker interactions. Thus the activated carbon in the purifier also has a finite lifetime and must be periodically replaced.

Therefore, the ideal small, lightweight AC/PP filter for this application would normally be readily consumed by a stream of contaminants and quickly be deactivated, making the filter require frequent replacement, or be impractically large with unreasonable pressure drops for the HVAC system in order to maintain effectiveness for time frames on the order of months to a year.

However, the previously described versions of the present invention greatly reduce the purifier capacity limitation by combining the technologies into a single unit where the chamber with UV light and titanium dioxide that produces hydroxyl radicals provides a load reduction on the reactive media lifetime. This occurs through multiple mechanisms.

The first effect is that contaminants in the air first encounter the open reaction chamber 20 where contaminants react and are oxidized by the continuous supply of hydroxyl radicals. This reduces the load on the purifier by removing contaminants that would react with the potassium permanganate. This allows the potassium permanganate to primarily be used when heavily contaminated air is present, extending its lifetime.

Secondly, complete oxidation of components reduces them to carbon dioxide and water, two components which do not strongly adhere to activated carbon, thus extending the lifetime of the activated carbon. When the air does not contain contaminants, the hydroxyl radicals will reach adsorbed contaminants on the activated carbon and potassium permanganate and may react, causing the adsorbed contaminant to react into $CO_2$ and water, thereby regenerating the reactive media and allowing for increased total capacity. This invention therefore provides a passive increase to the lifetime of the purifier media through proper design of the unit, while proper placement in the HVAC system prevents radicals from entering the home.

While the present invention reduces the load and provides extended lifetime, there are contaminants that will not be oxidized (e.g., silicates) that will eventually coat the purifier. Therefore, while extending the lifetime, the purifier will still need to be periodically replaced. However, the reduction in purifier size directly corresponds to a reduction in the pressure drop across the whole unit, enabling a lower impact on the overall HVAC system.

While we have shown and described several implementations in accordance with the disclosure, it should be understood that the same is susceptible to further changes and modifications without departing from the scope of our disclosure. Therefore, we do not want to be limited to the details shown and described herein but intend to cover all such changes and modifications as are encompassed by the scope of the appended claims.

What is claimed is:

1. A single unit in-duct air purification device for insertion into ductwork or duct board proximate an air handler of a residential HVAC system for reducing and removing air contaminants, comprising:
    an open hexahedron chamber having two open surfaces opposite one another, a first side surface securing a purifier, a second side surface securing two ultra-violet C (UV-C) lamps and an electrical ballast, a third side surface opposite the first side surface and is a baffled surface covered with a $TiO_2$ coating, and fourth side surface opposite the second side surface that secures the first side surface and third side surface together;
    wherein the first side surface is formed as a pair of rails and the purifier is an activated carbon potassium permanganate (AC/PP) purifier and the purifier is mounted in the pair of rails;
    wherein the UV-C lamps are positioned between the first side and the third side, and further wherein the UV-C lamps are closer to the third side in order for ultraviolet light emitted from the UV-C lamps to irradiate the $TiO_2$ coating and causes the $TiO_2$ coating to react with moisture in the air to make hydroxyl (OH) radicals which will then react and oxidize contaminants into products of carbon dioxide and water;
    wherein the electrical ballast is connected to the two UV-C lamps and attached to the second side that is a flange to support the device when mounted in the ductwork proximate the air handler in the residential HVAC system, and wherein the second side contains an access plate that is removable so that the purifier can be removed and replaced without having to remove the device from the ductwork;
    and
    wherein the rails of the first side are fastened to the fourth side and the third side is fastened to the fourth side.

* * * * *